United States Patent [19]

Fleming et al.

[11] 4,067,951

[45] Jan. 10, 1978

[54] PROCESS FOR MAKING IMPEDANCE MEASURING MODULE

[75] Inventors: James H. Fleming, Palo Alto; Melvin Rudin, Los Altos, both of Calif.

[73] Assignee: Bactomatic Inc., Palo Alto, Calif.

[21] Appl. No.: 633,213

[22] Filed: Nov. 19, 1975

[51] Int. Cl.² .............................................. B29D 3/02
[52] U.S. Cl. .................................. 264/272; 264/275; 264/279; 264/334
[58] Field of Search ............... 264/272, 334, 328, 275, 264/279

[56] References Cited

U.S. PATENT DOCUMENTS

| | | | |
|---|---|---|---|
| 3,311,690 | 3/1967 | Fischer | 264/328 X |
| 3,641,254 | 2/1972 | Bunting | 264/272 X |
| 3,668,779 | 6/1972 | Turner | 264/272 X |
| 3,671,621 | 6/1972 | Fukuoka | 264/334 X |
| 3,712,575 | 1/1973 | Bement | 264/272 X |
| 3,896,545 | 7/1975 | MacTurk | 264/272 X |
| 3,963,822 | 6/1976 | Beck | 264/272 X |

*Primary Examiner*—Richard R. Kucia

*Attorney, Agent, or Firm*—Phillips, Moore, Weissenberger, Lempio & Majestic

[57] ABSTRACT

The invention is concerned with an injection mold for making a plastic impedance measurement module having a generally flat metal grid imbedded in the plastic thereof with a plurality of pairs of electrodes upstanding generally perpendicularly from said grid, one pair into each of a plurality of chambers, said electrodes being uncoated by said plastic.

The process comprises placing the grid adjacent a first mold half of an injection mold with the electrodes each within a respective one of a plurality of slots extending into the first mold half, the first mold half having a first generally flat recessed portion defining a top surface of a base of the module and a plurality of channels extending from the first portion into the first mold half defining the plurality of chambers. The process further includes bringing together the first mold half and a second mold half having a second generally flat usually non-recessed portion for forming the injection mold, first support means extending from the second portion supportingly contacting the grid and injecting plastic into the mold to form the module.

5 Claims, 13 Drawing Figures

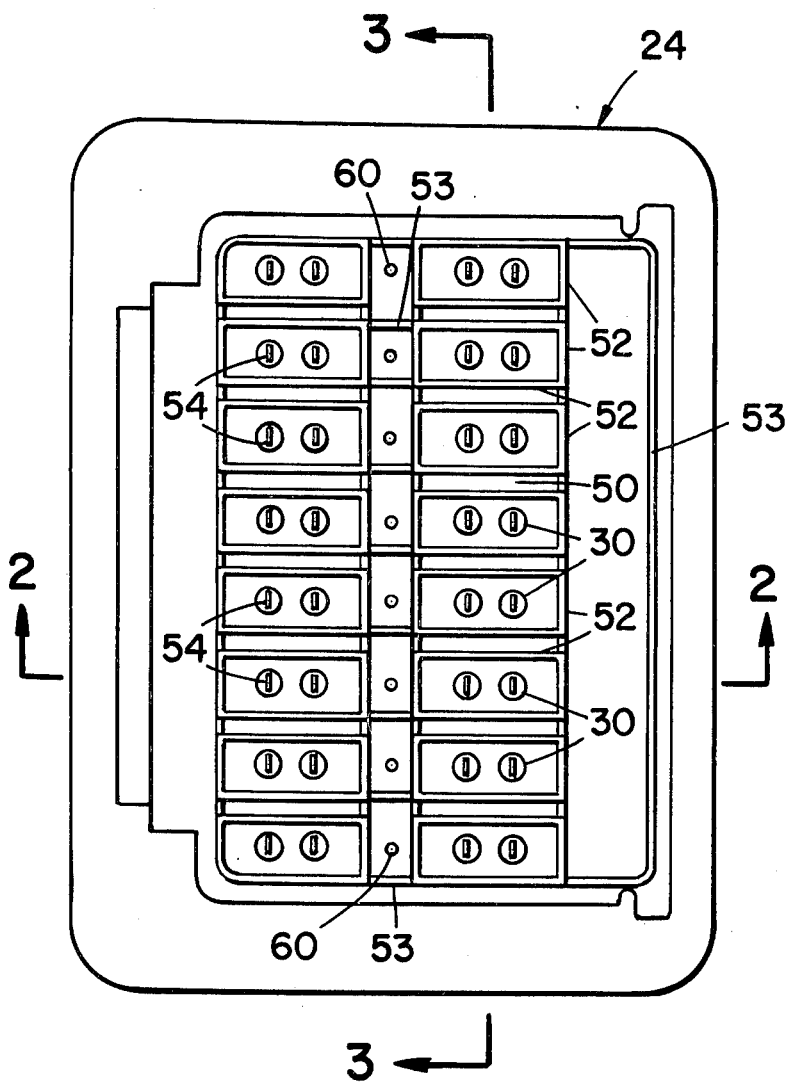
FIG_1
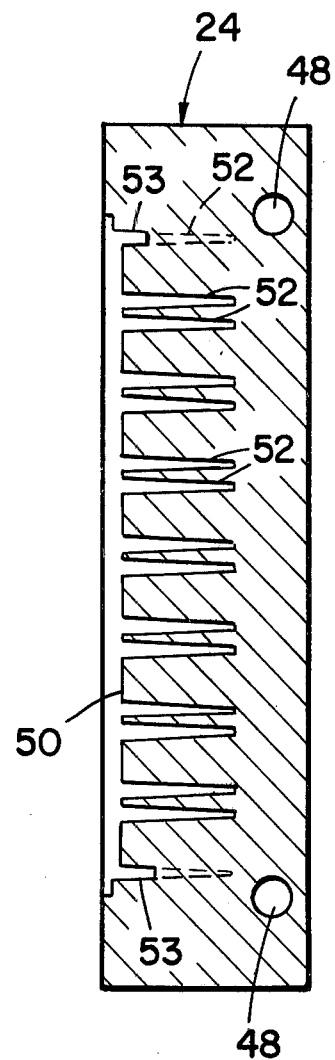
FIG_3
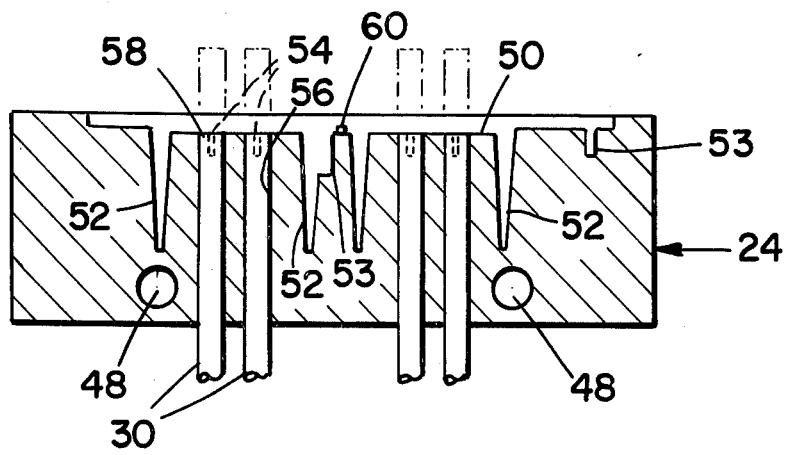
FIG_2

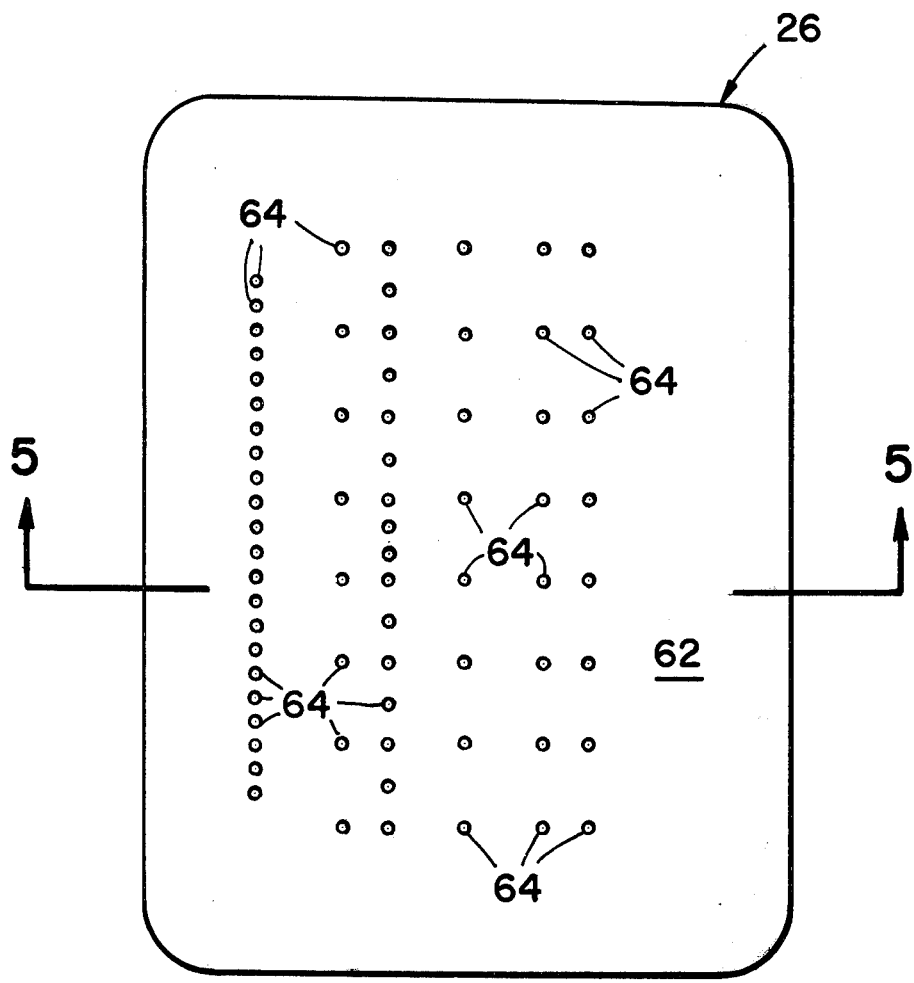
FIG_4
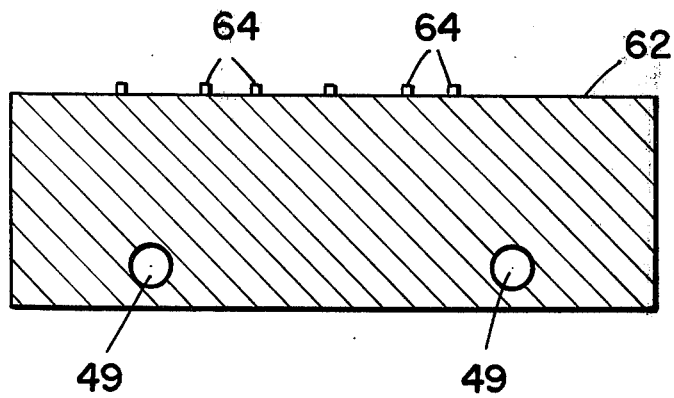
FIG_5

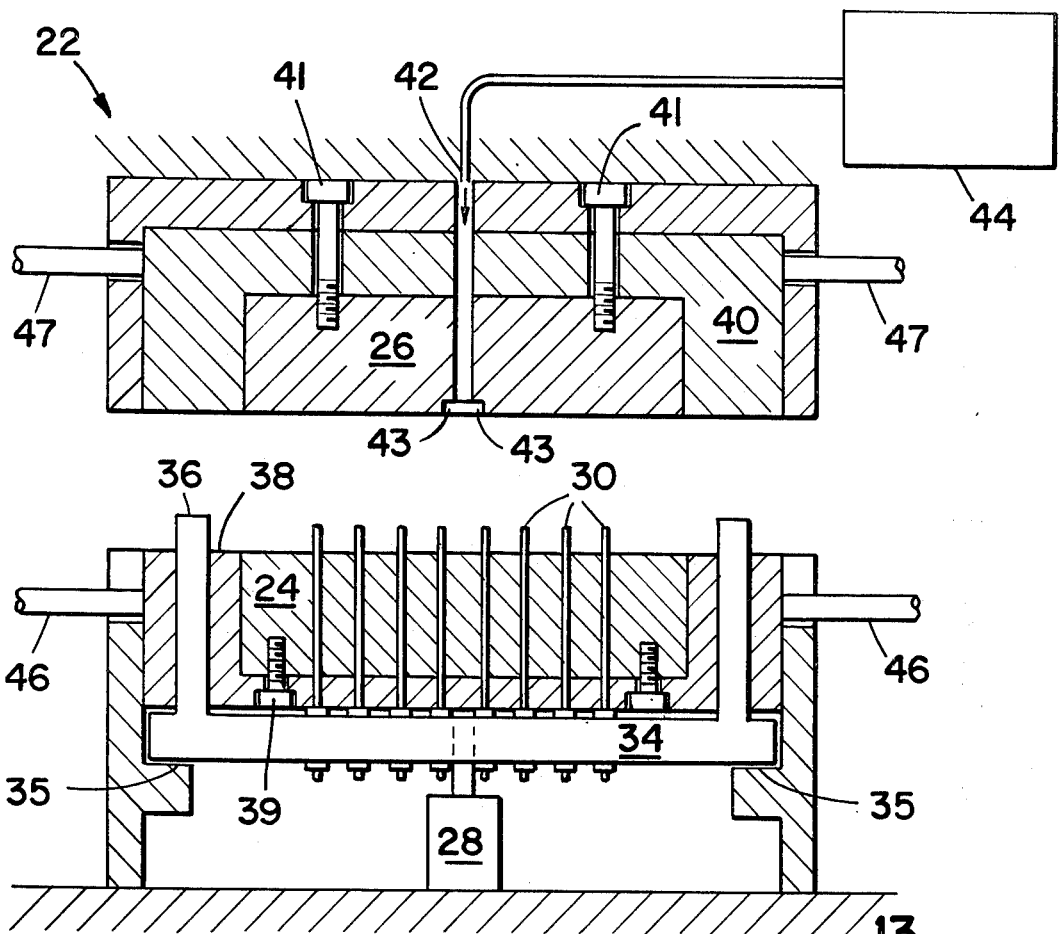
FIG_6
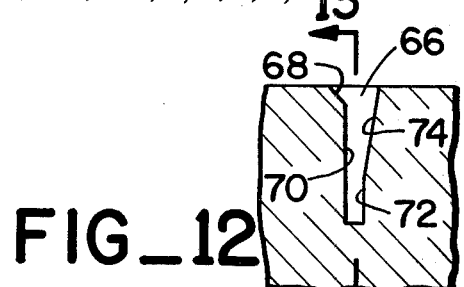
FIG_12
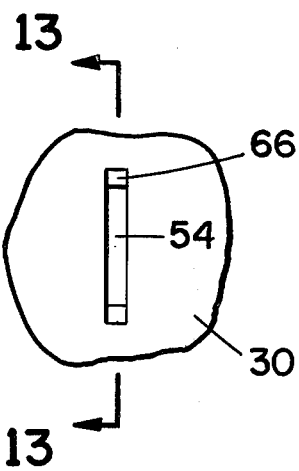
FIG_10
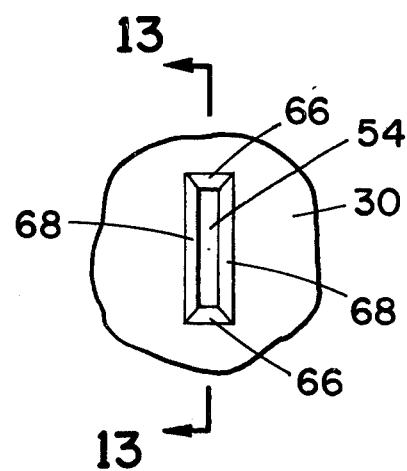
FIG_11
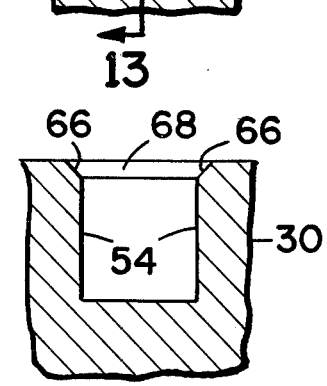
FIG_13

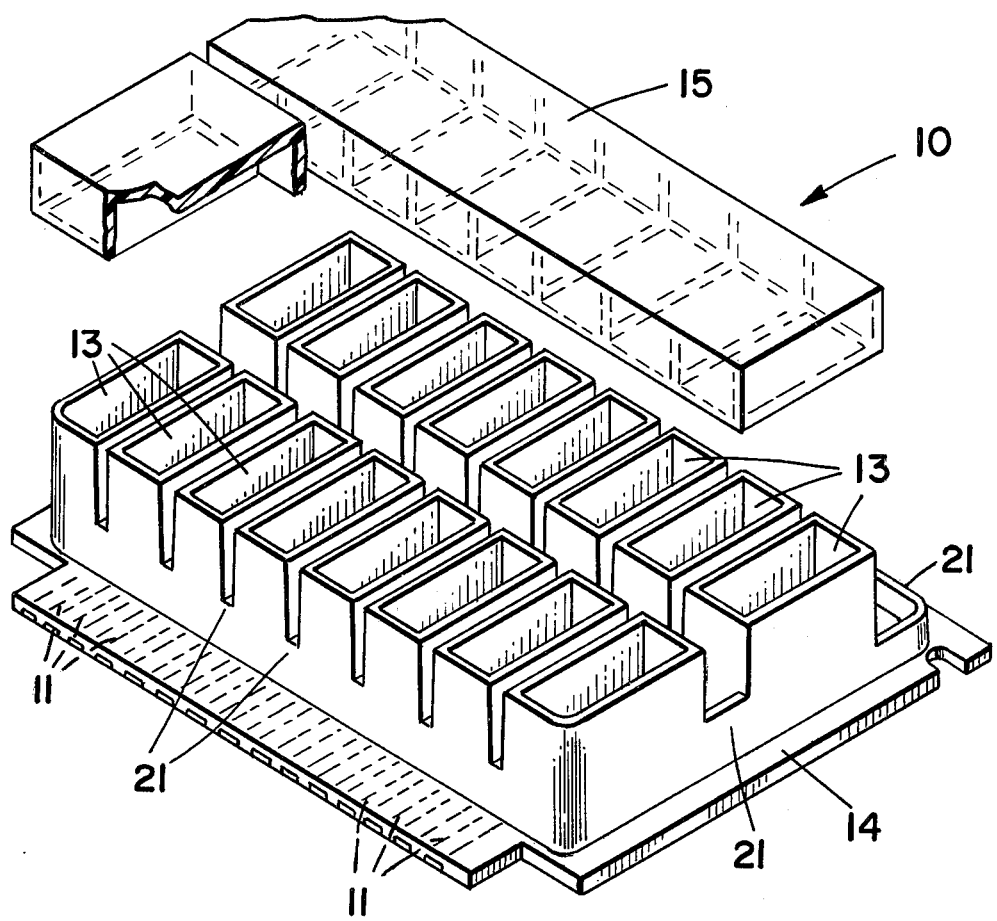
FIG_7
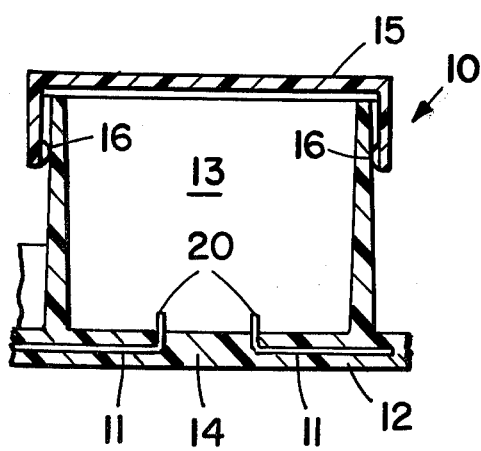
FIG_8
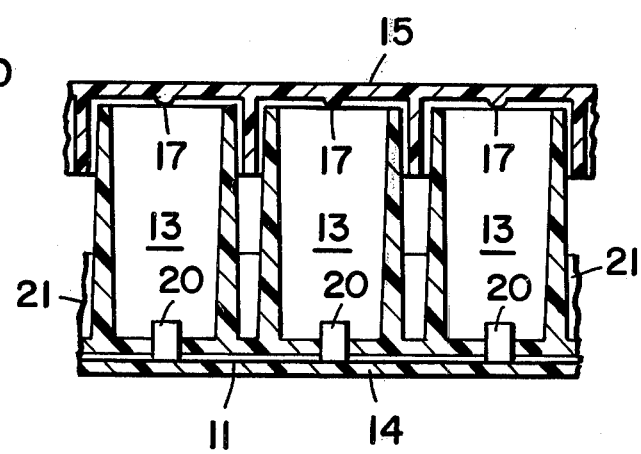
FIG_9

PROCESS FOR MAKING IMPEDANCE MEASURING MODULE

BACKGROUND OF THE INVENTION

1. Field of the Invention

The invention is concerned with the field of injection molding, and more particularly with the field of injection molding as applied to the formation of impedance measuring modules. More particularly yet, the invention is concerned with the formation via injection molding of an impedance measuring module with a metal grid completely imbedded in plastic with the exception of the leads thereof and of a pair of pluralities of electrodes, one pair of electrode within each chamber or cell of the impedance measuring module.

2. Prior Art

The use of electrode containing measuring cells to determine whether or not microorganisms are present in samples injected in said cells through measurements of changes in impedance therein is known as described for example in U.S. Pat. No. 3,743,581, commonly assigned herewith. The use of impedance measuring modules which have a plurality of cells upraised therefrom is also known as taught for example in U.S. Pat. No. 3,890,201, also commonly assigned herewith. In the latter patent, the modules are formed from circuit board-like boards having the conductors upraised therefrom and plastic modules or the like are glued or otherwise fastened in place atop the conductors on said boards whereby a pair of electrodes are exposed to the interiors of the chambers formed on the boards. Such modules are not readily adaptable to rapid mass production methods and, further, since the metal conductors atop such boards are exposed they may be fairly easily damaged through rough handling and the like.

Accordingly, the present invention is concerned with the formation of impedance measuring modules wherein a metal conducting grid within the module is substantially completely imbedded in plastic to protect it from harm. The production of such modules has, however, created certain problems unique to the design of the modules. Most particularly, it has been necessary to design an injection mold wherein a metal grid can be properly placed therein and yet wherein the electrodes which extend from the grid can be protected from coating by the plastic injected into the injection mold so that the impedance between these electrodes and, accordingly, any changes in the impedance between these electrodes can be accurately measured.

Accordingly, having realized the problems inherent in adapting injection molding techniques to formulating impedance measuring modules, the present invention provides a particular mold design and a particular injection molding process which allows for the mass production of impedance measuring modules with the electrodes therein free of plastic and properly spaced from one another yet with the grids thereof otherwise generally imbedded in plastic. The mold and process of the present invention thus provide fast and inexpensive operation available with injection molding along with substantially complete imbedding of the conducting member of the module so as to protect it from bending, scratching and the like.

SUMMARY OF THE INVENTION

In one sense, the invention comprises an injection mold for making a plastic impedance measurement module having a generally flat metal grid imbedded in the plastic thereof with a plurality of pairs of electrodes upstanding generally perpendicularly from said grid, one pair into each of a plurality of chambers, said electrodes being uncoated by said plastic. The mold comprises a first mold half having a first generally flat generally recessed portion defining a top of a base of the module and a plurality of channels extending from the first portion into the first mold half defining the plurality of chambers and including a plurality of pairs of spaced apart slots extending from the base into the first mold half, one of the pairs of the slots extending into each of the chambers for accepting and preventing coating of the electrodes. The mold further includes a second mold half having a second generally flat usually non-recessed portion for mating with the first portion to form the injection mold, the second portion having support means extending therefrom towards the first portion for supporting and positioning the grid. Means are also provided for moving the first and second mold halves together and apart and means are provided for injecting plastic between the mold formed by bringing together the first and second mold halves.

In another sense the invention comprises an injection molding process for making a plastic impedance measurement module having a generally flat metal grid imbedded therein with a plurality of pairs of electrodes upstanding generally perpendicularly from the grid, one pair into each of a plurality of chambers, the electrodes being uncoated by the plastic. The process comprises placing the grid adjacent a first mold half of an injection mold with the electrodes each within a respective one of a plurality of slots extending into the first mold half, the first mold half havig a first generally flat generally recessed portion defining a top of a base of the module and a plurality of channels extending from the first portion into the first mold half defining the plurality of chambers. The process further comprises bringing together the first mold half and a second mold half having a second generally flat generally non-recessed portion for forming the injection mold, first support means extending from the second portion supportingly contacting the grid and injecting plastic into the mold to form the module.

BRIEF DESCRIPTION OF THE DRAWINGS

The invention will be better understood by reference to the figures of the drawings wherein like numbers denote like parts throughout and wherein:

FIG. 1 illustrates in plan view a first mold half of the injection mold of the invention;

FIG. 2 illustrates a view taken along the line 2—2 of FIG. 1;

FIG. 3 illustrates a view taken along the line 3 — 3 of FIG. 1;

FIG. 4 illustrates in plan view a second mold half of the injection mold of the present invention;

FIG. 5 illustrates a view taken along the line 5 — 5 of FIG. 4;

FIG. 6 illustrates in side elevation view a mold of the present invention including means for moving the first and second mold halves together and apart and means for injecting plastic therebetween;

FIG. 7 in partial perspective and FIGS. 8 and 9 in partial view, in section, illustrate a plastic impedance module with a grid imbedded therein having electrodes upstanding generally perpendicularly therefrom, one pair into each of a plurality of chambers forming a part thereof;

FIGS. 10, 11 and 12 illustrate alternate embodiments of the slots which form a part of the mold of the present invention; and FIG. 13 illustrates a view taken along the line 13—13 of any of FIGS. 10, 11 and 12.

DETAILED DESCRIPTION OF A PREFERRED EMBODIMENT

Referring first to FIGS. 7, 8 and 9 there is illustrated a plastic impedance measurement module 10 comprising a metal grid 11 imbedded in a plastic matrix 12, said plastic matrix 12 including a plurality of chambers 13 upraised from a base portion 14 which includes imbedded therein the metal grid 11. A single cap 15 covers several of the chambers 13 and both a tight snap fit and an air space are assured between the cap 15 and the chambers 13 by a plurality of side detents 16 and a plurality of ridges 17. A plurality of pairs of electrodes 20 are upstanding generally perpendicularly from the metal grid 11, one pair of electrodes being upstanding within each of the chambers 13 generally perpendicularly to the rest of the metal grid 11. The module also includes a plurality of support walls 21 for added strength and rigidity. The present invention is concerned with the injection molding of a module such as 10.

Turning now to FIG. 6 there is illustrated an injection molding apparatus 22 in which a mold is formed for injection molding by bringing together a first mold half 24 and a second mold half 26 under pressure. Means are provided for moving the first and second mold halves together and apart. The particular means illustrated comprise a hydraulic cylinder 28 which serves to move the first mold half 24 into contact with the stationary second mold half 26. For reasons which will later become apparent a portion of the first mold half 24, namely a plurality of rods 30 are made movable relative to the first mold half 24 as by the hydraulic cylinder 28 causing a movable plate 34 (a so-called stripper plate) to which the rods 30 are removably attached to contact stopping blocks 35. Also attached to the movable plate 34 are generally a plurality of upstanding members (return bars) 36 which move along with the rods 30 and generally exceed the rods 30 in length by a distance equal to the thickness of the base portion 14 of the module 10 and which serve to take the brunt of the force as the first mold half 24 is moved towards the second mold half 26 under the impetus of the hydraulic cylinder 28. The first mold half 24 is held in a first form 38 as by bolts 39 therefor and the second mold half 26 is likewise held in a second form 40 therefor as by bolts 41. Means are provided for injecting plastic into the mold formed by the first and second mold halves 24 and 26 when they are together. The means illustrated in FIG. 6 comprise a passageway 42 and side passages 43 connected to a plastic supply source 44. The plastic supply source 44 provides plastic under pressure to the passageway 42 which plastic then flows between the first mold half 24 and the second mold half 26. The mold halves 24 and 26 are maintained at desired temperature as by circulating coolant and/or heating fluids to the first form 38 and the second form 40 via conduits 46 and 47 respectively. The fluids flow into the respective mold halves via the passageways 48 and 49, respectively.

Turning now most particularly to FIGS. 1-3 the first mold half 24 is illustrated in detail. As will be noted, the first mold half 24 has a first generally flat recessed portion 50 which when the first mold half 24 is mated with the second mold half 26 defines the top of the base 14 of the module 10. The first mold half 24 further includes a plurality of channels 52 extending from the first portion 50 into the body of said first mold half 24. The channels 52 define the plurality of chambers 13 of the module 10. A plurality of wall channels 53 also extend from the first portion 50 into the body of the first mold half 24 to define the support walls 21. As will be noted by reference to FIGS. 1-3, the first mold half 24 includes a plurality of pairs of spaced apart slots 54 extending from the first portion 50 into the body of the first mold half 24 with one of the pairs of slots 54 extending into each of the chambers 13 defined by the channels 52, the slots 54 serving to accept and prevent coating of the upstanding electrodes 20 extending from the metal grid 11.

In the preferred embodiment as illustrated in FIGS. 1-3 the first mold half 24 includes the plurality of rods 30 in a plurality of passages 56 therein. The rods 30 fit slidingly but tightly within the passages 56. The slots 54 are formed each in a respective top end 58 of a respective one of the rods 30. As will be noted most particularly by reference to FIGS. 2 and 6 the rods 30 are movable generally perpendicularly to the first portion 50. As is shown most particularly in phantom in FIG. 2 the rods 30 are extendable outwardly from the first portion 50 and generally towards the second mold half 26. The means for extending the rods outwardly from the first portion 50 can be as illustrated in FIG. 6 the hydraulic cylinder 28 in combination with the stopping blocks 35, which when the movable plate 34 is stopped thereagainst continues to propel the first form 38 and thereby the first mold half 24 relative to the rods 30.

Referring now particularly to FIGS. 1 and 2 the first mold half 24 can preferably include support means for example a first plurality of pins 60 extending generally from the first recessed portion 50 to support the metal grid 11 at a plurality of positions each external of the chambers 13 of the module 10 which is to be formed within the mold of the invention.

Turning most particularly to a consideration of the rods 30 it will be seen that they serve several purposes. First, the slots 54 can be easily and accurately formed therein as by using carbon electrodes or the like to burn the slots 54 into the top ends 58 thereof. Second, the rods 30 can be made of a very hard metal as compared with the metal of the rest of the first mold half 24 thereby assuring that the slots 54 will maintain their shape through numerous contacts with the electrodes 20 of the metal grid 11. This is important since the electrodes 20 must fit snugly within the slots 54 to prevent their being coated with plastic. Generally the fit is of the order of 0.001 inch or better. Further, the rods 30 are replaceable should they become damaged in any way. Still further, the rods 30 can be used as ejector pins to eject the finally molded modules 10 upon opening of the injection molding apparatus 22. Another advantage of using the rods 30 is that they can be advanced to above the first portion 50, as shown in phantom in FIG. 2 and as shown in FIG. 6, whereby the metal grid 11 can be placed atop the rods 30 with the electrodes 20 within respective slots 54. This operation away from the portion 50 protects it and other parts of the mold half 24 from scuffing or the like which might occur through contact with the metal grid 11 if it is positioned with the electrodes 20 thereof into the slots 54 with the rods 30 retracted as shown in the solid lines of FIG. 2. This operation also saves the time needed for closing and opening the mold one time per cycle of the molding operation. Also, operating above the mold allows relative ease and speed of operator placement of the metal grid 11 with the electrodes 20 within the slots 54. The slots 54 of course serve to accept and prevent coating of the electrodes 20. This is essential to the production of modules which are useful for accurate impedance measurement since, of course, if the surfaces of the electrodes were completely imbedded in plastic no current could flow and if some of the electrodes were partially coated in plastic the impedance measurements would be dependent upon the relative areas of the exposed electrodes.

Turning now primarily to FIGS. 4 and 5 there is illustrated the second mold half 26. As will be noted, the second mold half 26 has a second generally flat generally non-recessed portion 62 for mating with the first portion 50 to form an injection mold. The second portion 62 has support means extending therefrom towards the first portion 50 for supporting the grid 11. In the embodiment illustrated in FIGS. 4 and 5 the support means comprises a second plurality of pins 64. Generally, in order to supply necessary rigidity and alignment of the metal grid 11 and to correct for any bending or the like therein the second plurality of pins 64 will include pins aligned to be adjacent each of the upstanding electrodes 20. A substantial number of additional pins will generally also form a part of the second plurality of pins 64 since it is primarily the second plurality of pins 64 which serves to properly align the metal grid 11 so that it will be enclosed in the plastic matrix 12. The first plurality of pins 60 along with the top ends 58 of the rods 30 serve in combination with the second plurality of pins 64 to very rigidly and exactly position the metal grid 11 prior to insertion of plastic from the plastic supply source 44 to form the plastic matrix 12.

The slots 54 shown in FIGS. 1 and 2 are simple right rectangular parallelepipeds in shape. FIGS. 10, 11 and 12 illustrate three alternate embodiments of the present invention wherein chamfers of different types are added to the slots 54 to aid in fast placement of the electrodes 20 therein thus allowing faster molding operation. FIG. 13 illustrates a view of the chamfers which are common to each of the embodiments illustrated in FIGS. 10, 11 and 12.

Turning to the embodiment of FIG. 10, a 45° end chamfer 66 is formed on each end of the slot 54 of the rod 30 to guide a respective one of the electrodes 20 therein. The end chamfer 66 proceeds only a short way down the slot 54 to prevent plastic coating of the electrode 20.

Turning next to the embodiment of FIG. 11, the 45° end chamfer 66 is formed on each end of the slot 54 of the rod 30 and also, a 45° side chamfer 68 is formed on each side of the slot 54. The side chamfers 68 also proceed only a short way down the slot 54, again to prevent coating of the electrode 20.

Turning finally to the embodiment of FIG. 12, the shallow 45° end chamfer 66 is formed on each end of the slot 54 of the rod 30 and also, a single shallow 45° end chamfer 68 is formed on a first side 70 of the slot 54 which faces the pairing slot 54 within a respective one of the chambers 13. On a second side 72 of the slot 54 a second smaller angle chamfer 74 proceeds a significant way, but less than all the way, e.g., 60% or so, down the slot 54. When plastic is injected it thus fills in the smaller angle chamfer 74 blocking off a significant portion of the non-facing sides of each pair of electrodes 20. Since most current flows between facing sides of the pairs of electrodes 20 this does not deleteriously effect their operation. It is important that the smaller angle chamfer 74 does not proceed to the bottom of the slot 54 as the second side 72 of said slot 54 must serve to force the facing side of each electrode 20 into close contact with the first side 70 of said slot 54 to prevent plastic coating of said facing side.

The use of the chamfers 66, 68 and/or 74 as set out above leads to the formation of a fillet of plastic about the electrodes 20 generally where they pass into the base 14. This can provide an added advantage in holding the plastic against the metal grid 11 adjacent the electrodes 20 thus helping to minimize or eliminate any tendency for leakage to occur about said electrodes 20 due to plastic shrinkage, lack of sufficient metal-plastic adhesion and the like.

As will be apparent, when chamfers are used on the slots 54 the angle of the chamfer is basically only a simple design choice. Thus, the angles of the chamfers can vary quite significantly from 45°.

Process

The operation of the injection molding process and mold of the present invention for making a plastic impedance measurment module 10 having the first generally flat metal grid 11 imbedded therein with the plurality of pairs of electrodes 20 upstanding generally perpendicularly from the grid 11, one pair in each of the plurality of chambers 13, the electrodes 20 being uncoated by the plastic is relatively apparent from the preceeding description but will be described in detail at this time to aid in a full understanding of the invention.

First, with the mold halves 24 and 26 apart the grid 11 is placed adjacent the first mold half 24 of the injection molding apparatus 22 with the electrodes 20 each within a respective one of the plurality of slots 54 which extend into the first mold half 24. The first mold half 24 as previously mentioned has the first generally flat portion 50 thereof which serves to define the top of the base portion 14 of the module 10 after plastic has been injected into the mold formed by the first mold half 24 and the second mold half 26 to form the module 10. The metal grid 11 can be placed with the electrodes 20 in the slots 54 with the rods 30 advanced so their top ends 58 are removed from the first recessed portion 50 of the first mold half 24. Alternately, the rods 30 can have their top ends 58 adjacent the first portion 50 when the metal grid 11 is put in place.

Second, the first mold half 24 is brought together with the second mold half 26 under the impetus of the hydraulic cylinder 28 so that the second portion 62 mates with the first portion 50 thus forming the injection mold. The second plurality of pins 64 impinge upon the metal grid 11 on the side thereof removed from the electrodes 20 and thus serve to position the metal grid 11. The first plurality of pins 60 serve as support means for supportingly contacting the metal grid 11 on the side thereof which includes the electrodes 20. Thus, the metal grid 11 is held between the first mold half 24 and the second mold half 26 and more particularly between the first portion 50 and the second portion 62 with the electrodes 20 within the slots 54 and with the rods 30 having their top ends 58 adjacent the first portion 50.

Third, plastic is then inserted from plastic supply source 44 or the like via passageway 42 and side passages 43 in a conventional manner into the injection molding apparatus 22 to form the module 10. Any plastic suitable for injection molding may be used to form the modules 10. Preferably, the plastic is of the clear variety and is relatively rigid. For example polystyrene may be utilized as the plastic. Alternatively somewhat less rigid plastic such as polypropylene may be used. The upstanding members 36 generally take the main thrust of the first mold half 24 as it is propelled towards the second mold half 26 thus preventing harsh contact of the two mold halves with each other or with the metal grid 11 therebetween.

Fourth, the first and second mold halves 24 and 26 part under the impetus of the hydraulic cylinder 28.

Fifth, the movable plate 34 contacts the stopping blocks 35 while the first mold half 24 continues to move away from the second mold half 26 thus causing the rods 30 to eject the module 10.

Sixth, the module 10 is removed. In one mode of operation as explained above a new metal grid 11 is placed with its electrodes 20 in the slots 54 of the rods 30 and the second through sixth steps set out above are repeated. In another mode of operation as also explained above the mold is closed and then opened to place the top ends 58 of the rods 30 adjacent the first portion 50 of the first mold half 24 and then the second through sixth steps set out above are repeated.

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. An injection molding process for making a plastic impedance module having a generally flat metal grid imbedded therein with a plurality of pairs of electrodes upstanding generally perpendicularly from said grid, one pair into each of a plurality of chambers, said electrodes being uncoated by plastic, comprising:

placing said grid adjacent a first mold half of an injection mold with said electrodes inserted each within a respective one of a plurality of slots, each of said slots being within a top end of a rod movable within a hole generally perpendicularly to a first generally flat portion defining a top of a base of said module, said first mold half having a plurality of channels extending from said first portion into said first mold half defining said plurality of chambers;

propelling together said first mold half and a second mold half having a second generally flat portion for forming said injection mold, pin means extending from said first and second generally flat portions of said first and second mold halves supportingly contacting said grid on both sides thereof;

injecting plastic into said mold to form said module with all of said grid other than the points of contact of said pins on both sides of said grid and said electrodes thereby forming said module; and removing said module from said mold.

2. A process as in claim 1, wherein said placing step comprises:

advancing said rods upwardly from said flat portion in said first mold half and positioning said grid against said rods with said electrodes each held within a respective one of said slots.

3. An injection molding process for making a plastic impedance measurement module having a generally flat metal grid imbedded therein with a plurality of pairs of electrodes upstanding generally perpendicular from said grid, one pair into each of a plurality of chambers, said electrodes being uncoated by said plastic, comprising:

supporting said grid on a first surface thereof by a plurality of fixed pins extending from a generally flat portion of a first mold half of an injection mold;

inserting said electrodes each within a slot extending into a top end of one of a plurality of rods slidably movable in said first mold half, said movement being generally perpendicular to said flat portion;

mating a second mold half withh said first mold half to form said mold wherein said grid is positioned between opposing mold halves;

supporting said grid on a second surface thereof, opposite said first surface by a plurality of fixed pins extending from a generally flat portion of said second mold half;

injecting plastic into said mold to cover all of said grid other than the points of contact of said pins on both sides of said grid and said electrodes thereby forming said module; and removing said module from said mold.

4. A process as in claim 3, wherein said inserting step comprises:

advancing said rods outwardly from said flat portion in said first mold half and positioning said grid against said rods with said electrodes each held in a respective one of said slots.

5. A process as in claim 4, wherein said removing step include ejecting said module from said mold halves by moving said rods outwardly from said flat portion in said first mold half.

* * * * *